(12) United States Patent
Psyanin (10) Patent No.: US 9,474,480 B2
(45) Date of Patent: Oct. 25, 2016

(54) DEVICE FOR THE PAINLESS AND MINIMALLY INVASIVE PARENTERAL ADMINISTRATION OF PHARMACEUTICAL PREPARATIONS AND SAMPLING OF BLOOD

(76) Inventor: Aleksandr Stanislavovich Psyanin, Moscow (RU)

( * ) Notice: Subject to any disclaimer, the term of this patent is extended or adjusted under 35 U.S.C. 154(b) by 0 days.

(21) Appl. No.: 14/236,409

(22) PCT Filed: Jul. 24, 2012

(86) PCT No.: PCT/RU2012/000607
§ 371 (c)(1),
(2), (4) Date: Mar. 27, 2014

(87) PCT Pub. No.: WO2013/019149
PCT Pub. Date: Feb. 7, 2013

(65) Prior Publication Data
US 2014/0221926 A1    Aug. 7, 2014

(30) Foreign Application Priority Data
Aug. 1, 2011    (RU) ................................. 2011131946

(51) Int. Cl.
*A61M 5/155* (2006.01)
*A61B 5/155* (2006.01)
(Continued)

(52) U.S. Cl.
CPC ............. *A61B 5/155* (2013.01); *A61B 5/1427* (2013.01); *A61B 5/1438* (2013.01);
(Continued)

(58) Field of Classification Search
CPC ................ A61B 5/155; A61B 5/1427; A61B 5/150068; A61B 5/150106; A61M 5/425; A61M 5/422; A61M 5/427
See application file for complete search history.

(56) References Cited

U.S. PATENT DOCUMENTS 5,167,630 A    12/1992    Paul
5,969,754 A    10/1999    Zeman
(Continued)

FOREIGN PATENT DOCUMENTS

EP    1064035 B1    11/2003
EP    2 168 481 A1    3/2010
(Continued)

OTHER PUBLICATIONS

RU Search Report, RU, Apr. 9, 2012, OOO Foras Lab.
(Continued)

*Primary Examiner* — Bradley Osinski (57) ABSTRACT

A device for invasive parenteral administration of pharmaceutical preparations and sampling of blood consists of: a cuff, a mounting frame for accommodating a sliding disc that consists of a movable front disc half and a movable rear disc half, said rear disc half being provided with a channel for accommodating a cassette cartridge for a cassette with needles; a vial of anaesthetic; and a scanning device. Upon compression of the disc halves, the scanning device locates a vein, a signal is given off, and the disc halves lock in the appropriate position. The needle is introduced into the blood stream by pressing on the lid of the cassette. The lid slides back and the tip of a syringe or of the cannula of a blood transfusion system or of the cannula of an evacuated blood sample container is introduced via a hermetic aperture situated beneath the lid.

1 Claim, 12 Drawing Sheets

(51) Int. Cl.
*A61M 5/42* (2006.01)
*A61B 5/15* (2006.01)
*A61B 5/151* (2006.01)
*A61B 5/154* (2006.01)
*A61M 5/24* (2006.01)
*A61B 5/00* (2006.01)
*A61B 5/022* (2006.01)

(52) U.S. Cl.
CPC ........ *A61B 5/154* (2013.01); *A61B 5/150053* (2013.01); *A61B 5/150068* (2013.01); *A61B 5/150106* (2013.01); *A61B 5/15113* (2013.01); *A61B 5/15146* (2013.01); *A61B 5/150748* (2013.01); *A61B 5/425* (2013.01); *A61M 5/422* (2013.01); *A61M 5/427* (2013.01); *A61B 5/02233* (2013.01); *A61B 5/15003* (2013.01); *A61B 5/489* (2013.01); *A61B 5/742* (2013.01); *A61B 5/7405* (2013.01); *A61M 5/24* (2013.01); *A61M 2205/581* (2013.01); *A61M 2205/583* (2013.01)

(56) References Cited

U.S. PATENT DOCUMENTS

| 6,074,364 | A | 6/2000 | Paul |
| 2007/0016069 | A1 | 1/2007 | Grunwald et al. |
| 2007/0123803 | A1 | 5/2007 | Fujiwara et al. |

FOREIGN PATENT DOCUMENTS

| SU | 1134199 A | 1/1985 |
| WO | 99/48546 A1 | 9/1999 |

OTHER PUBLICATIONS

European search report for EP 12820737.0 mailed May 22, 2015.

SECTION D-D
SCALE 2 : 1

DEVICE FOR THE PAINLESS AND MINIMALLY INVASIVE PARENTERAL ADMINISTRATION OF PHARMACEUTICAL PREPARATIONS AND SAMPLING OF BLOOD

RELATED APPLICATION INFORMATION

This application is a 371 of International Application PCT/RU2012/000607 filed 24 Jul. 2012 entitled "Device For The Painless And Minimally Invasive Parenteral Administration Of Pharmaceutical Preparations And Sampling Of Blood", which was published on 7 Feb. 2013 with International Publication Number WO 2013/0191419 A1 and which claims priority from Russian Patent Application 2011131946, filed 1 Aug. 2011, the content of which are incorporated herein by reference.

The present invention relates to painless and low invasive parenteral administration of pharmaceutical preparations and blood sampling.

BACKGROUND OF THE INVENTION

The invention may be used in medical institutions and is also suitable for personal use according to the above purpose.

A number of analogs of the claimed device are commercially available.

In particular, Site-Rite 5 (available from BARD Access, US) is known, which is a special ultrasound scanner for catheterization of central veins, provided with a linear multi-frequency 5-11 MHz sensor and a guidance puncture needle. This set (ultrasound scanner, sensor) costs over 1 million rubles.

Known is a device provided with a piezosensor disposed within a needle bore, wherein the Doppler effect is used to find the venous bed (US Patent Application No. 2007-0016069). Under visual inspection of a medical technician, transdermal puncture is performed whereafter the blood flow direction is identified using light and sound indications on an external device. However, since the ultrasonic beam and the needle have the same directivity, the so called "needle yawing" occurs. After the vein has been found, it is punctured. The sensor is then removed from the vein bore and further manipulations are performed.

The disadvantages of this device include:
painful sensations felt until the vein is found;
probable formation of an air gap within the needle between the sensor and the tissues so that the sensor operation is disturbed;
the sensor may be used only once;
uncased sensor cannot be used due to its unstable operation as a result of becoming clogged with the pieces of tissues from the space between the needle walls and the plate itself or complete non-conductibility to the dense tissues because of an air cushion;
high cost of the case-type sensor.

In addition, known is a so called Vein Viewer device available from Christie (U.S. Pat. No. 5,969,754), wherein based on a difference in absorptivity between the skin and the veins due to the presence of hemoglobin in the former, veins are detected by means of the IR technique and visualized on an illuminated projection directly onto the area under study thereby facilitating the task. This technique was originally used for verification of the so called "venous ID" and its inherent complete authenticity of a human. This device may only be operated by skilled professionals and physicians, is intended for use at hospitals and is expensive (25,000 USD). Similar equipment is also used by AccuVien (priced at 6,900 USD).

This device is the closest prior art.

The disadvantages of all the above cited prior art devices include:
precision targeting of the needle is impossible to puncture the vein due to the presence of the "human factor" because the needle is introduced by a human operator;
the laser aperture has to be positioned exactly at an angle of 90 degrees to the vein to avoid the lateral image shift resulting in presentation of a "virtual" vein whose projection disagrees with the actual vein;
the "actual" vein size may differ since unless the laser aperture is at 18 cm from the skin surface, a "play of projection" occurs;
no pre-anesthesia is provided in the device as such;
a high cost of the device.

BRIEF SUMMARY OF THE INVENTION

The claimed device differs from the prior art primarily in the following:
the procedure of administering the pharmaceutical preparation is painless and low-invasive;
pre-anesthesia is provided;
the vein bore is hit with a high accuracy (above 99.9%);
the "human factor" is minimized;
injections may be made without assistance;
lower production costs;
a low "injection" cost.

The claimed device comprises a basic modification composed of a set including a cuff similar to the cuff for measuring the arterial tension, a fastening frame, a slide disk, a needle holder cartridge, an anesthetic flask, a scanning device and a light and/or sound component.

The needle holder, the needle holder cartridge and the anesthetic flask tube are all disposable.

The cuff is designed such that a built-in scanning device for locating the vein is arranged therein. It is programmed to determine the vein thickness and depth. The scanning device and the light and/or sound component are not the subject matter of the present invention.

The cuff comprises a strip of fabric for wrapping around the patient's arm and fixing thereon. Fixation may be accomplished by various means.

In particular, fixation may be accomplished by pumping of air into the flat soft bag inside the cuff. However, pumping is limited by the air pressure (not more than 60 mm Hg).

The cuff ends may by connected to each other for example using a Velcro-type fastener.

A working cutout for arranging the fastening frame therein is provide in the cuff.

The fastening frame is a rectangle provided on the inner part of its longitudinal side with stepwise teeth holding the slide disk. The frame lower part arranged from the patients' arm side is provided along its perimeter with a projecting edge immediately contacting the patient's arm surface. In the recess formed between the frame inner edge and the projecting edge, a lower edge of the slide disk is arranged. On one of the transversal sides of the frame, a receiver bushing is provided with a through hole in the form of a bore, truncated from the patient's arm side, and a fastening projection on the outer side of the bushing for holding and fastening the anesthetic flask. The frame is further provided with working holes arranged in pairs, with connection grooves formed therein for fastening the frame to the cuff.

The slide disk arranged within the fastening frame is made of two half-disks, a front one and a rear one. In a free state, the half-disks are kept at distance from one another by spring-loaded members. This design allows the disks to be removed and replaced and also to cause the disk to move along the frame and to rotate around its own axis since when the two half-disks are pressed together, the slide disk teeth disengage from the frame teeth. The lower part of the half-disks is provided with stepwise teeth for engaging the half-disks in the fastening frame. The half-disks have a base provided with a projecting lower edge. The rear half-disk is formed with a bore for receiving the holder cartridge. On the inner walls of the bore for receiving the cartridge, fixing teeth are formed engaging the teeth on the cartridge clips. Within an end projection of the rear half-disk, a bore is formed for receiving the scanning device.

The rear half-disk is provided with an end projection with two cylindrical holes on its sides with threaded connections for receiving a screw and a helical spring-loaded member received by an end recess of the front half-disk. An end portion of the front half-disk is also provided with two through holes with a widening at the outer side for receiving the countersunk screw heads and with a widening at the inner side for receiving the helical spring-loaded member. The holes in the rear and front half-disks are arranged coaxially and the screw length is selected such that when the half-disks move toward each other, the screw head will be slightly projecting from the hole so that the front half-disk motion will be only limited by the screw head. The screw is connected to the rear half-disk with a threaded connection. Clamping pads are arranged on the opposite side of the slide disk assembly.

Within the rear half-disk, a bore is formed for receiving the holder cartridge serving as a housing for the needle holder and comprising a chamfered end parallelepiped provided with a contact edge arranged at the point of contact with the skin and having a polymeric material attached thereto and hermetically sealing the hole. Clips with locks are arranged at the cartridge edges and the cartridge interior comprises a circular through hole with a thrust pad forming a truncated cylindrical bore along the inner walls of which guides are arranged for the holder ridges to prevent its rotation around its axis and also to fix the teeth for engaging the holder teeth.

The holder is a cylindrical element provided on its outer side with ridges for the holder cartridge guides, large and small fixing teeth engaging the teeth on the inner side of the holder cartridge, a sealed cover, a working saw cut ending with a projection and operable to limit the linear motion of the holder within the cartridge, wherein from the cylindrical element end directed toward the arm and beveled at an angle, a plurality of microneedles of a uniform length projects in communication with an internal receptacle by means of the bores passing into a common bore whose upper part widens to form a flared end, and wherein the points of microneedles form a visual plane parallel to the chamfered end of the holder provided with the sealed cover having a cone-shaped plug.

The anesthetic flask attached to the transversal side of the fastening frame using the receiver bushing with the through hole comprises a flask tube and an adapter which are connected by means of a threaded connection. The flask tube comprises a housing formed as a ridged cap with a cylindrical hollow projecting receptacle for anesthetic with a thread provided on the outer side thereof and a membrane on the end portion thereof. The adapter is provided with a cylindrical cell having a hollow puncture needle inside directed toward the membrane of the flask tube when connected. On the opposite side of the adapter, a bushing is arranged with a bore for anesthetic and on the outer portion, a lock is arranged for fastening to the receiver bushing of the fastening frame.

The cuff is applied to the patient's arm, in particular to the cubital vein (bend of elbow) and is fixed on the arm by any known method. In doing so, the working cutout with the fastening frame and the slide disk are located above the bend of elbow. The slide disk is caused manually to move along the fastening frame with the aid of clamping pads of the slide disk and to this end, the half-disks are pressed together and the fixing teeth on the half-disks disengage from the teeth on the fastening frame.

The detection of a vein by the scanning device sensor is recorded by means of a light and/or sound indication. Clamping of the half-disks is ceased and the slide disk is held in place.

The medical staff or the patient himself places the anesthetic flask onto the fastening frame.

The cartridge with the needle holder is inserted into the bore for receiving the slide disk cartridge. The set composed of the cartridge and the holder is taken out of a sealed sterile package and is disposable.

The anesthetic flask is screwed in so that the puncture needle punctures the receptacle and the anesthetic is sprayed onto the holder cartridge film. The film provides antisepsis and protects the microneedles against contact with the anesthetic.

After a few seconds, pressure is applied to the holder whose motion is strictly limited to the anatomic features of the human arm veins and is assicated with the vein indication process. As the holder moves, the needle penetrates the circulatory bed.

The scanning device sensor is selectively tuned to particular blood vessels, their size, wall thickness and depth. At the same time, the needle length is selected in a direct dependence with the indicating capabilities of the sensor.

Upon penetration the circulatory bed, the finger pad of the holder is turned back and via the cone-shaped widening of the sealed cover wherein the cone-shaped plug was disposed under the pad, the syringe nozzle, the cannula of a blood transfusion system or the cannula of a blood sampling vacuum tube is inserted.

BRIEF DESCRIPTION OF THE DRAWINGS

FIG. 1 shows a general view of the device with the cuff, wherein
1 is a cuff;
2 is a fastening frame;
3 is a front half-disk;
4 is a rear half-disk;
5 is a holder;
6 is a holder cover;
47 is a flask adapter;
48 is a flask tube;
7 is a holder cartridge (with the holder cover drawn aside)

21 is a clamping pad of the front half-disk;
26 is a clamping pad of the rear half-disk;
27 is a lower edge of the rear half-disk;
28 are stepwise teeth of the rear half-disk;
29 is a bore for receiving the holder cartridge;
30 is a bore for receiving the scanning device;
FIG. 4 shows a sectional view of the slide disk, wherein
13 is a screw;
14 is a spring;
15 is an end recess;
16 is a cylindrical widening;
17 are through holes;
19 is a lower edge of the front half-disk;
20 are stepwise teeth of the front half-disk;
21 is a clamping pad of the front half-disk;
22 is a threaded connection;
23 is a cylindrical hole;
24 is an end projection;
26 is a clamping pad of the rear half-disk;
27 is a lower edge of the rear half-disk;
28 are stepwise teeth of the rear half-disk;
29 is a bore for receiving holder cartridge;
30 is a bore for receiving scanning device;
FIG. 5 shows a front view, a side view, a sectional view, a general view of the front half-disk, wherein
15 is an end recess;
16 is a cylindrical widening;
17 are through holes;
18 is a boundary groove;
19 is a lower edge;
20 are stepwise teeth;
21 is a clamping pad.

DETAILED DESCRIPTION OF THE INVENTION

The claimed device and the method for using the same will be described below with reference to the accompanying drawings.

Figure 1:
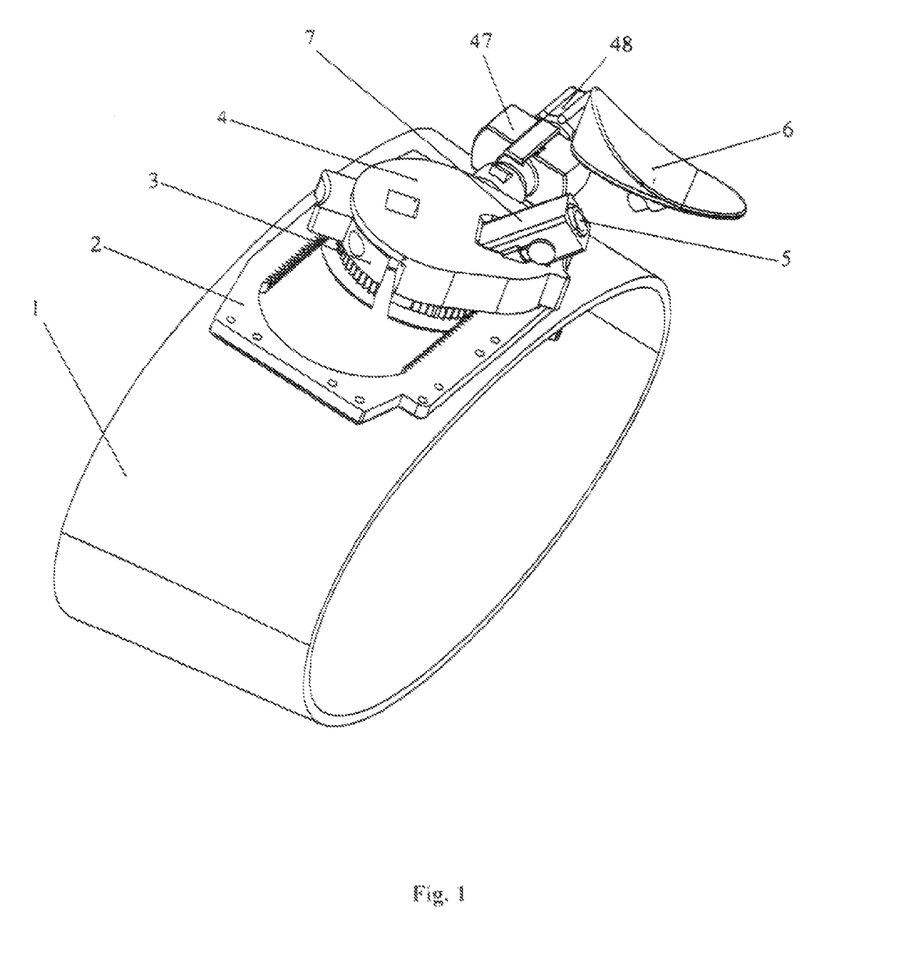
Figure 2:
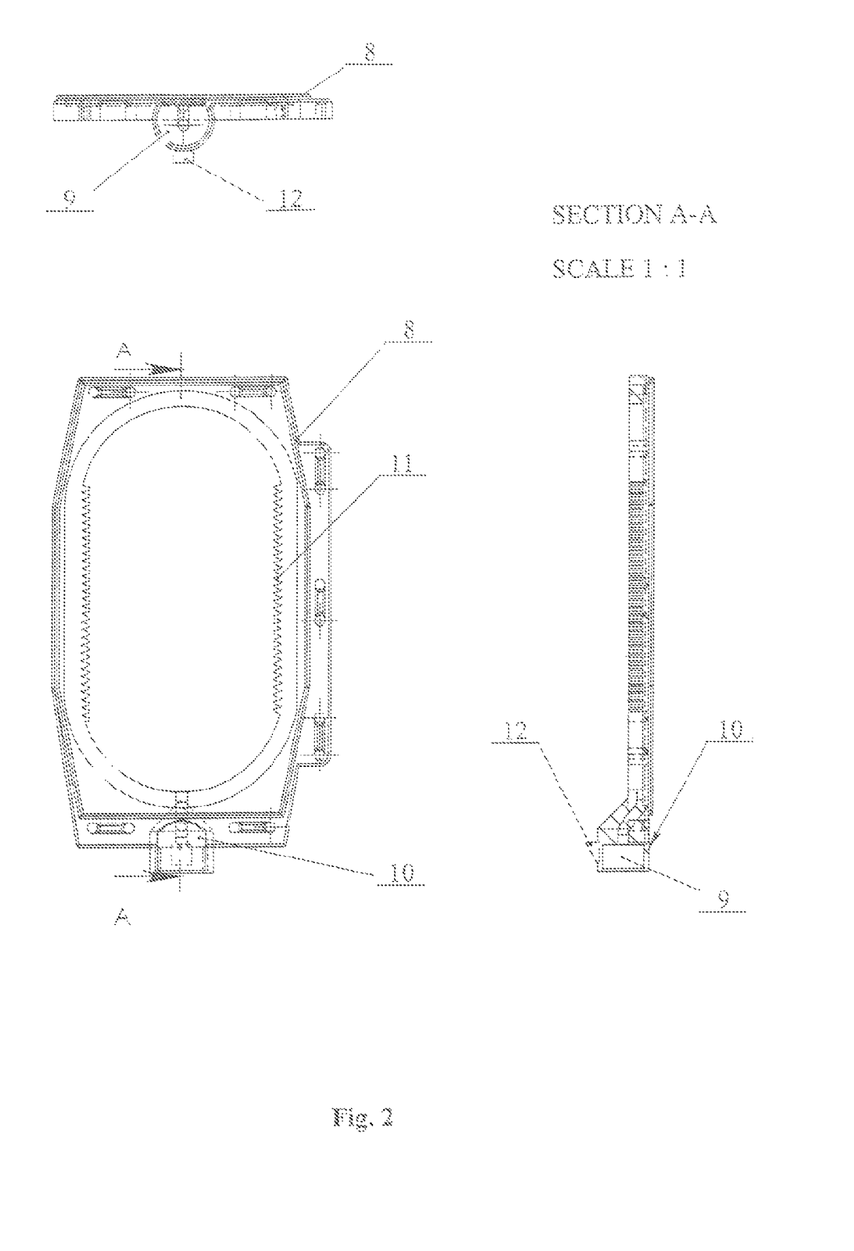
FIG. 2 shows a top view, a side view, a top sectional view of fastening frame, wherein
8 is a projecting edge;
9 is a receiver bushing;
10 is a bushing truncation;
11 are stepwise teeth of the fastening frame;
12 is a fastening projection.
Figure 6:
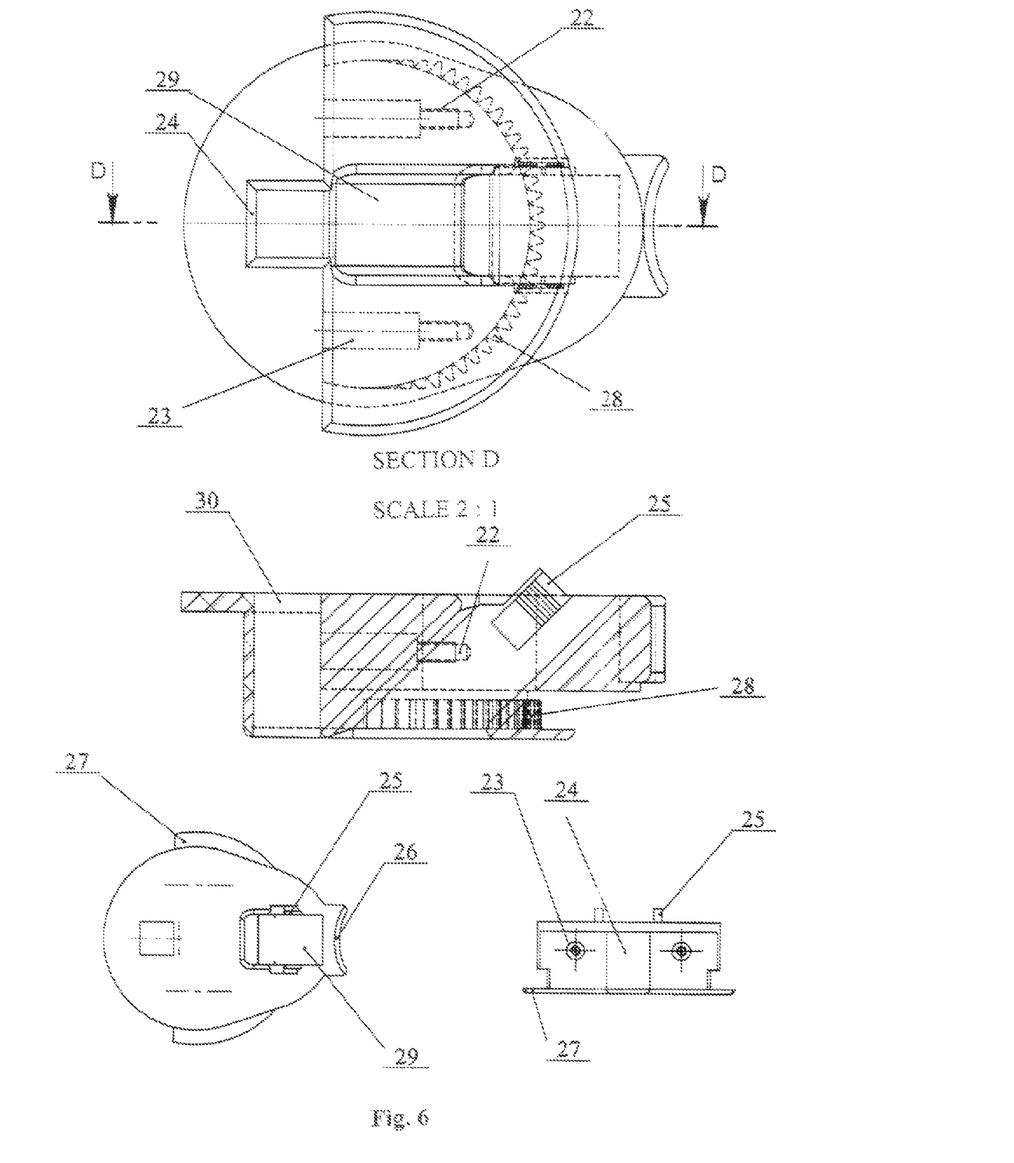
FIG. 6 shows a bottom view, a sectional side view, a top view, a front view of the rear half-disk, wherein
22 is a threaded connection;
23 is a cylindrical hole;
24 is an end projection;
25 are fixing teeth;
26 is a clamping pad;
27 is a lower edge;
28 are stepwise teeth;
29 is a bore for receiving the holder cartridge;
30 is a bore for receiving the scanning device.

The cuff 1 comprising a strip of fabric for fixing on the patient's arm is provided with a working cutout wherein the fastening frame 2 is disposed (FIGS. 1, 2) comprising a rectangle provided along the inner part of its longitudinal side with stepwise teeth (FIG. 2) for engaging the stepwise teeth 20 and 29 (FIGS. 5, 6), respectively, of the front and rear half-disks 3, 4 of the slide disk for fixing the slide disk within the fastening frame. Working holes with connection grooves are arranged in pairs in the frame 2 (FIG. 1) for fastening the same to the cuff 1 (FIG. 1).

Figure 3:
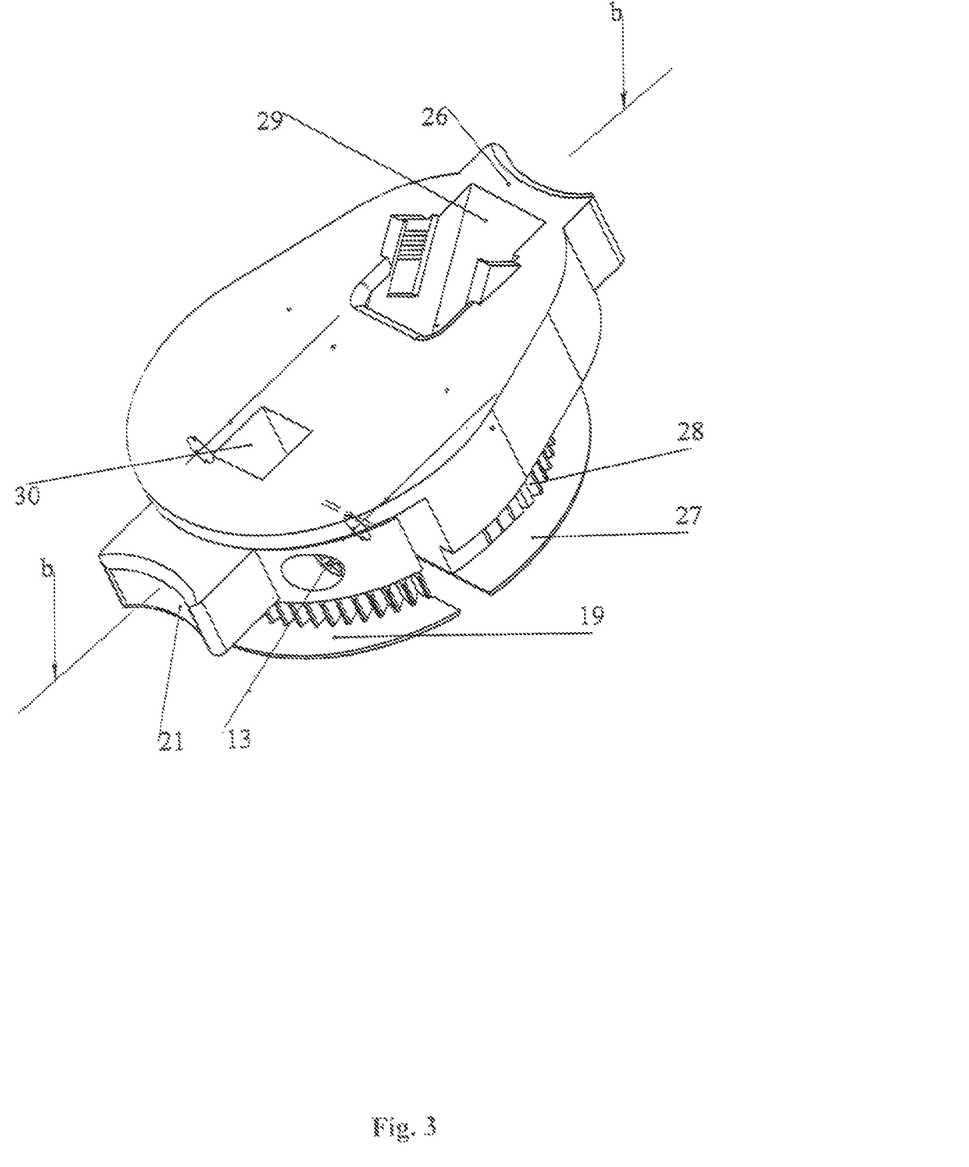
FIG. 3 shows a general view of the slide disk assembly, wherein
13 is a screw (screw head)
19 is a lower edge of the front half-disk.
Figure 4:
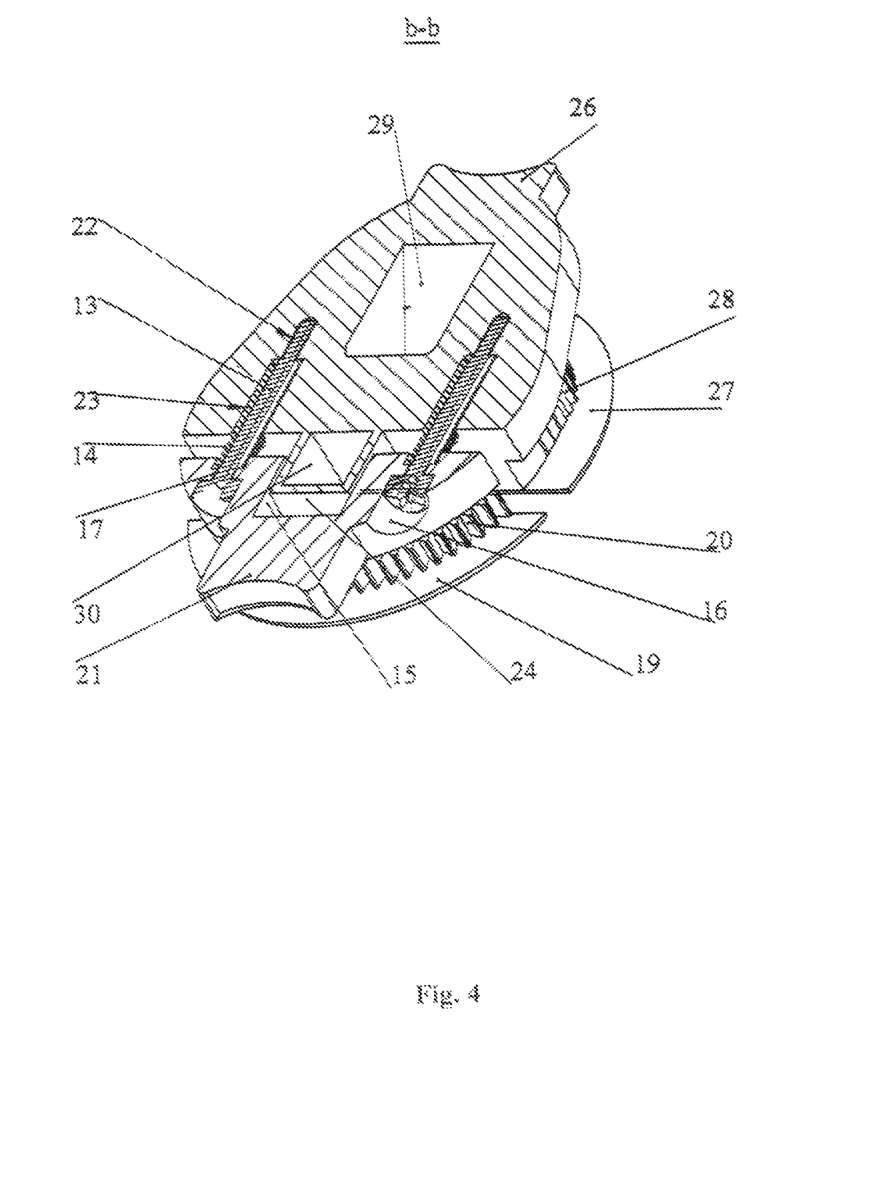

In a free state, the front and rear half-disks 3, 4 of the slide disk arranged within the fastening frame 2 (FIG. 1) are kept at a distance from one another by means of the spring-loaded members 14 (FIG. 4) and the screw 13 (FIG. 3, 4).

In the rear half-disk 4 (FIG. 1), the bore 29 (FIGS. 4, 6) is formed for receiving the holder cartridge 7 (FIGS. 1, 6) with the fixing teeth 25 (FIG. 6) arranged on its inner walls and engaging the fixing teeth 35 (FIG. 7) on the clips 31 (FIG. 7) of the holder cartridge 7 (FIG. 1, 7) comprising a parallelepiped with a skewed end on the side facing the arm and with the contact edge 34 (FIG. 7) having a polymeric material attached thereto to hermetically seal the hole. Clips 31 with locks 32 (FIG. 7) are arranged along the cartridge edge. The cartridge interior is formed as a circular through hole with the thrust pad 33 (FIG. 7) and guides for the holder ridges 37 (FIG. 8) to fix the small teeth 39 and the large teeth 40 (FIG. 8) of the holder 5 (FIG. 1). The holder cartridge 7 serves as a housing for the needle holder (FIGS. 1, 8).

The lower portion of the fastening frame 2 (FIG. 2) from the patient's arm side is provided along its perimeter with the projecting edge 8 (FIG. 2) contacting the patient's arm and is formed such that the lower edges 19 (FIGS. 3, 4, 5) and 27 (FIGS. 3, 4, 6) of the front and rear half-disks 3 and 4, respectively are arranged between the inner edges of longitudinal sides and the projecting edge 8. Furthermore, one of the transversal sides of the fastening frame 2 is provided with the receiver bushing 9 (FIG. 2) having a through hole in the form of the bore with the fastening projection 12 (FIG. 2) on the outer side for fastening the anesthetic flask (FIG. 9) consisting of the flask adapter 47 and the flask tube 48 (FIGS. 1, 9, 10, 11).

Figure 12:
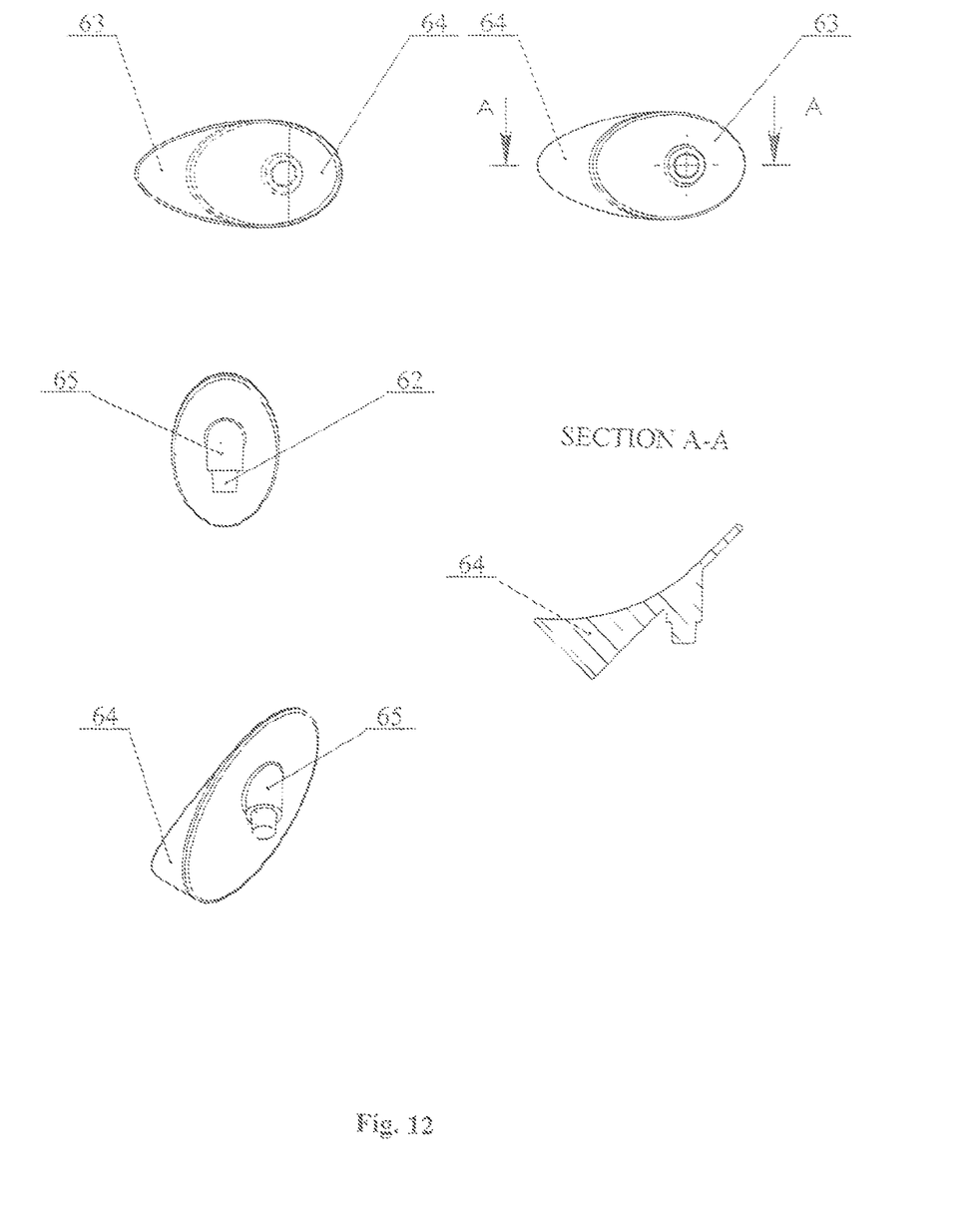
FIG. 12 shows a top view, a bottom view, a general view, a bottom axial view, a sectional view of the holder cover, wherein.
62 is a cone-shaped plug;
63 is a cover body (pad);
64 is lug on the cover body;
65 is a cylinder.

The needle holder (FIG. 8) comprises a cylindrical element provided on the outer side thereof with the ridges 37 (FIG. 8) for the guides of the holder cartridge 7, small fixing teeth 39 (FIG. 8) engaging the teeth 35 (FIG. 7) on the inner side holder cartridge 7, the sealed cover 6 with the cone-shaped plug 62 (FIG. 12), the working saw cut (FIG. 8) ending with the projection 42 (FIG. 8) and operable to limit the linear motion of the holder within the cartridge, wherein from the cylindrical element end directed toward the arm and beveled at an angle, a plurality of microneedles 43 (FIG. 8) of a uniform length projects in communication with the internal receptacle 44 (FIG. 8) by means of the bores passing into the common bore 45 (FIG. 8) whose upper part widens to form the flaring 46 (FIG. 8) with the cone-shaped plug 62 (FIG. 12) of the holder cover 6 (FIG. 1), and wherein the points of microneedles form a visual plane parallel to the chamfered end of the holder.

Figure 10:
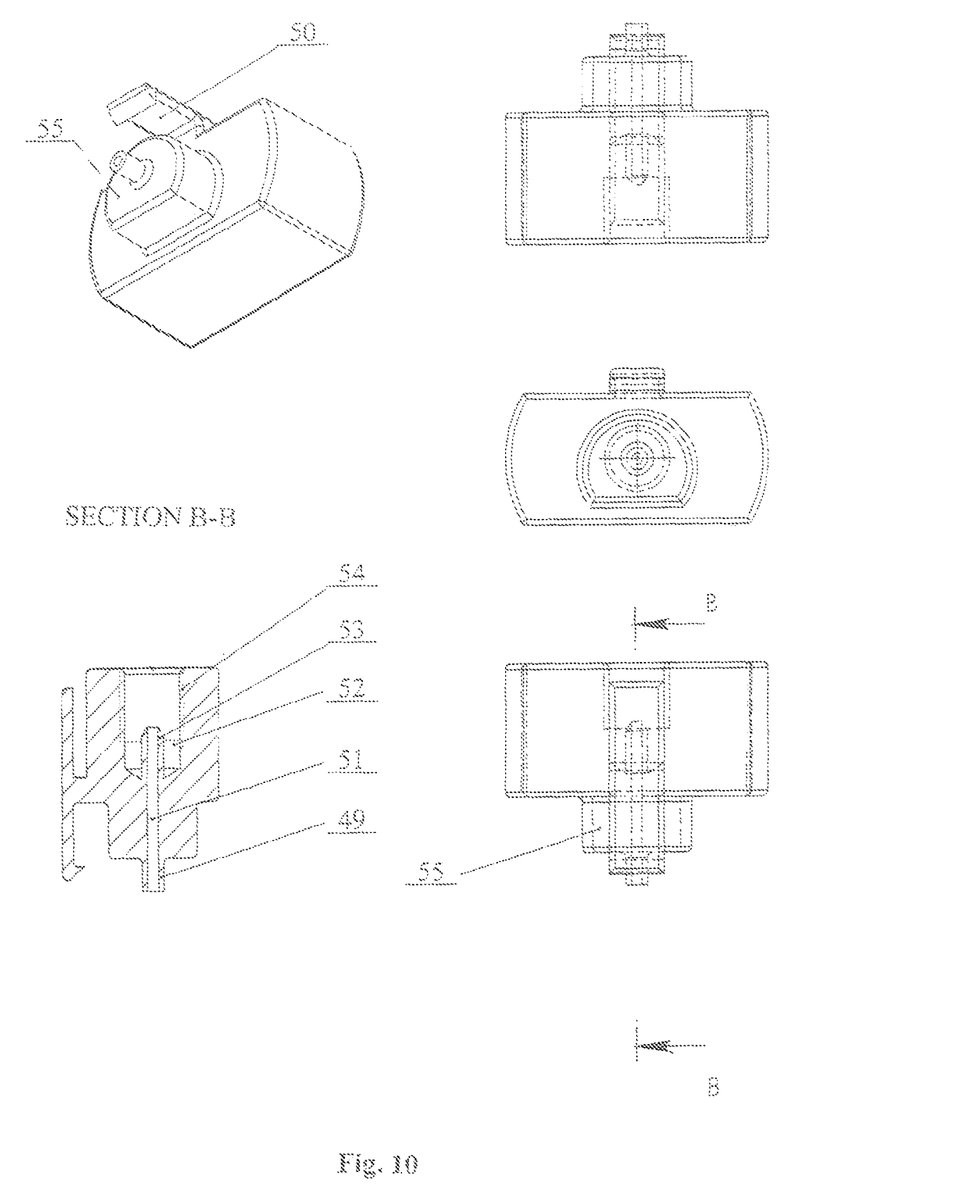
FIG. 10 shows a general sectional view, a bottom view, a front view, a top view of the flask adapter, wherein
49 is a tip;
50 is a lock;
51 is a bore for anesthetic;
52 is a cylindrical cell;
53 is a hollow needle;
54 is a thread;
55 is a bushing with a bore for anesthetic.
Figure 11:
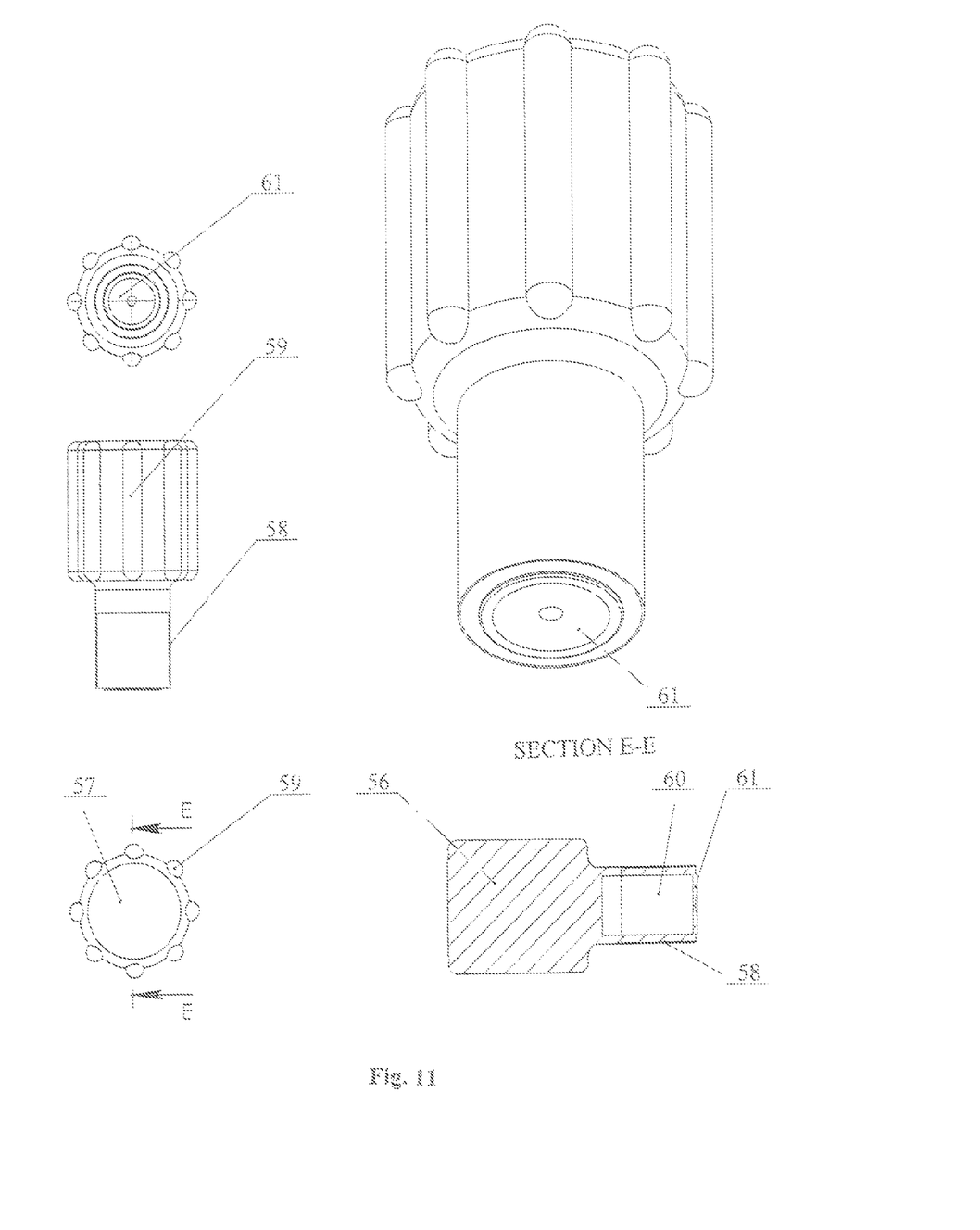
FIG. 11 shows a bottom view, a side view, a top view, a general sectional view of the flask tube, wherein
56 is a flask body;
57 is a cap;
58 is a thread;
59 is an edge;
60 is a receptacle;
61 is a membrane.

Attached to the transversal side of the fastening frame 2 using the receiver bushing 9 (FIG. 2) with a through hole, is the anesthetic flask comprising the flask tube 48 (FIG. 1, 9, 11) and the adapter 47 (FIGS. 1, 9, 10) which are connected by means of the threaded connection 54 (FIG. 10). The flask tube comprises the flask body 56 formed as the cap 57 (FIG. 11) with ridges 59 (FIG. 11) with the cylindrical hollow projecting receptacle 60 (FIG. 11) for anesthetic with the thread 58 (FIG. 11) provided on the outer side thereof and the membrane 61 (FIG. 11) on the end portion thereof. The adapter 47 is provided with the cylindrical cell 52 (FIG. 10) having the hollow puncture needle 53 (FIG. 10) inside directed toward the membrane 61 (FIG. 11) of the flask tube when connected. On the opposite side of the adapter, the bushing 55 (FIG. 10) is arranged with the bore 51 (FIG. 10) for anesthetic and on the outer portion, the lock 50 (FIG. 10) is arranged for fastening to the receiver bushing of the fastening frame 2.

As shown in FIG. 1, the cuff 1 is applied to the patient's arm, in particular to the cubital vein (bend of elbow) and is fixed. In doing so, the fastening frame 2 (FIG. 1) with the slide disk composed of the front and rear half-disks 3 and 4 (FIG. 1), respectively, is located above the bend of elbow. The frame lower portion arranged from the patient's arm side and provided along its perimeter with the projecting edge 8 (FIG. 2) directly contacts the arm surface.

The clamping pads 21, 26 (FIG. 4) of the front and rear half-disks 3, 4 (FIG. 1) are pressed manually with the aid of the spring 14 (FIG. 4) to press together the half-disks 3 and 4 so that the stepwise teeth 20 (FIGS. 4, 5) of the front half-disk and the stepwise teeth 28 (FIGS. 4, 6) of the rear half-disk disengage from the stepwise teeth 11 (FIG. 2) of the fastening frame 2 (FIG. 2) and cause the half-disks of the slide disk to move along the fastening frame.

The medical staff or the patient himself places the anesthetic flask (FIG. 9) comprising the tube adapter 47 and the flask tube 48 onto the fastening frame 2.

A set composed of the cartridge 7 (FIG. 1, FIG. 7) with the holders 5 (FIG. 1, FIG. 8) is inserted into the cartridge bore 29 (FIG. 4, 6) formed within the rear half-disk 4 (FIG. 1, 6) of the slide disk. The set is taken out of a sealed sterile package and is disposable.

Figure 7:
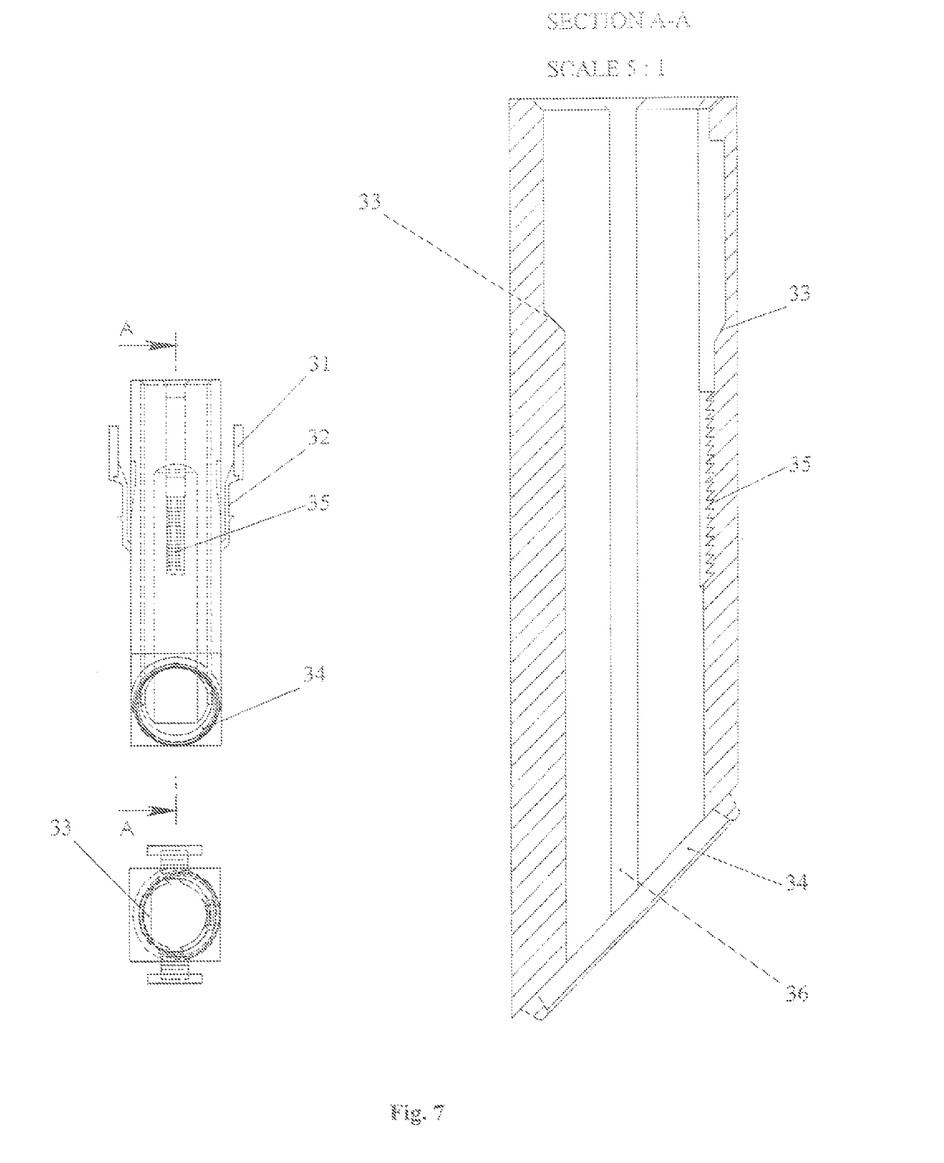
FIG. 7 shows a rear view, a top view, a sectional side view of the holder cartridge, wherein
31 is a clip;
32 is a lock;
33 is a thrust pad;
34 is a contact edge;
35 are fixing teeth;
36 are working slots.
Figure 8:
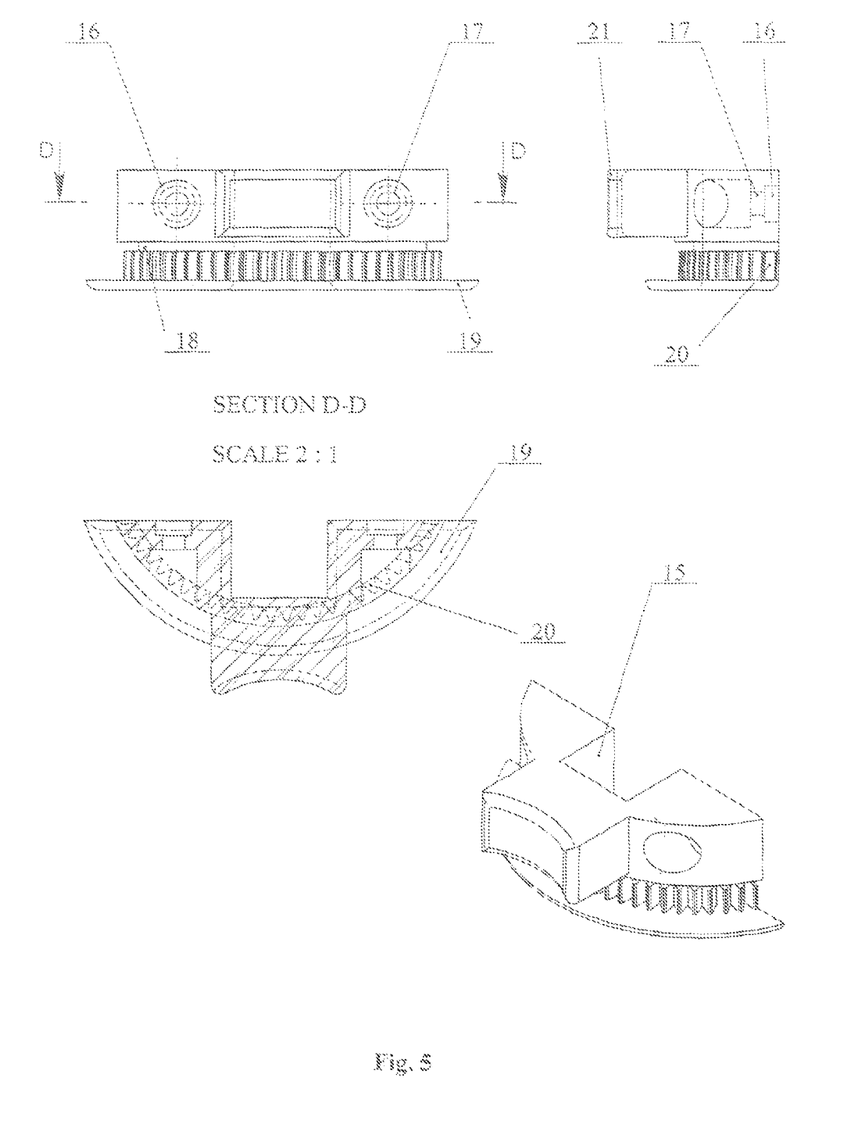
FIG. 8 shows a top view, a side view, a sectional rear view, a general view of the holder, wherein
37 is a ridge;
38 is a working recess;
39 is a small fixing tooth;
40 is a large fixing tooth;
41 is a working saw cut;
42 is a projection;
43 is a microneedle;
44 is an internal receptacle;
45 is a bore;
46 is a flaring.
Figure 9:
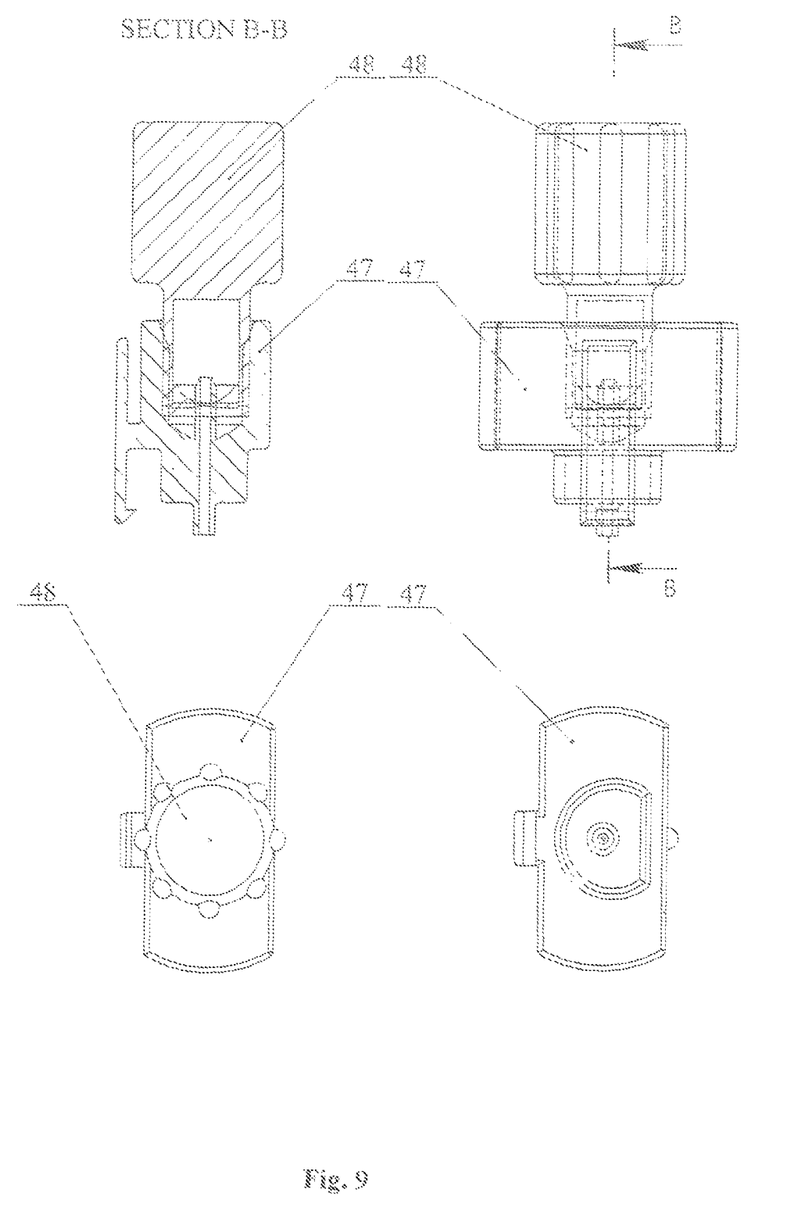
FIG. 9 shows a sectional side view, a general view, a top view, a front view of the flask assembly wherein
47 is a flask adapter;
48 is a flask tube.

The flask tube 48 (FIG. 9) with anesthetic is then screwed in so that the hollow puncture needle 53 (FIG. 10) punctures the receptacle 60 (FIG. 11) with anesthetic which is sprayed under the film (not shown in the Drawings) of the holder cartridge 7 (FIG. 7).

After a certain time required for the anesthetic to act, the cover 6 of the holder cartridge 7 (FIG. 1, 7) is pressed so that the holder 5 moves and the microneedles 43 (FIG. 8) penetrate the circulatory bed. The pad 63 (FIG. 12) is then turned back and via the cone-shaped sealed plug 62 (FIG. 12) under the pad 63, the syringe nozzle, the cannula of a blood transfusion system or the cannula of a blood sampling vacuum tube is inserted.

The invention claimed is:

1. A device for painless and low invasive parenteral administration of pharmaceutical preparations and blood sampling, including a cuff for wrapping around a patient's arm and fixing thereon, characterized in that the device comprises a fastening frame having arranged therein a slide disk with an anesthetic receptacle and a holder cartridge, said fastening frame disposed within a working cutout in the cuff and provided along longitudinal sides thereof with stepwise teeth for fixing the slide disk, a projecting edge along a perimeter of the frame contacting a patient's arm surface, wherein a recess formed between the projecting edge and an inner edge of the frame is intended to receive a lower edge of the slide disk, a receiver bushing on a transverse side of the frame with a through hole in a form of a bore, said receiver bushing being truncated from a patient's arm side, having a fastening projection on an outer side thereof for fixing and holding an anesthetic flask, and operable to receive the slide disk having a lower projecting edge and stepwise teeth for engaging the fastening frame and comprising a front half-disk with an end recess and a rear half-disk with an end projection received by the end recess of the front half-disk, and wherein both half-disks are provided with a thrust pad on opposite sides thereof, wherein the half-disks in a free state are kept at a distance from one another by spring-loaded members enabling their motion along the fastening frame, removal, replacement and ability to rotate around their own axis, a bore for receiving the holder cartridge with a needle holder provided with a sealed cover, the holder cartridge having on inner walls thereof fixing teeth engaging teeth on cartridge clips and formed as a parallelepiped with a skewed end provided with a contact edge with polymeric material hermetically sealing a hole at a point of contact with a skin, and an anesthetic flask comprising a flask tube with the anesthetic receptacle and a membrane on an end portion, an adapter with a cylindrical cell and a hollow puncture needle inside directed toward the flask tube membrane when connected, wherein on an opposite side of the adapter a bushing is arranged with a bore for anesthetic and on an outer portion a lock is arranged for fastening to the receiver bushing of the fastening frame, and a scanning device.

* * * * *